United States Patent
Knörl et al.

(10) Patent No.: US 8,418,001 B2
(45) Date of Patent: Apr. 9, 2013

(54) CONTEXT-RELATED TROUBLESHOOTING

(75) Inventors: Roland Knörl, Dormitz (DE); Franz Amon, Hessdorf (DE)

(73) Assignee: Siemens Aktiengesellschaft, München (DE)

( * ) Notice: Subject to any disclaimer, the term of this patent is extended or adjusted under 35 U.S.C. 154(b) by 240 days.

(21) Appl. No.: 11/937,008

(22) Filed: Nov. 8, 2007

(65) Prior Publication Data
US 2009/0125757 A1 May 14, 2009

(51) Int. Cl.
*G06F 11/00* (2006.01)
(52) U.S. Cl.
USPC .......... 714/47.1; 714/25; 714/46; 714/48
(58) Field of Classification Search ........... 714/46, 714/25, 48, 2, 31, 47.1
See application file for complete search history.

(56) References Cited

U.S. PATENT DOCUMENTS

| | | | |
|---|---|---|---|
| 6,859,893 B2* | 2/2005 | Hines | 714/38 |
| 7,162,406 B1* | 1/2007 | Dye | 703/21 |
| 7,852,337 B2* | 12/2010 | Archer et al. | 345/440 |
| 2004/0187048 A1* | 9/2004 | Angamuthu et al. | 714/27 |
| 2005/0223285 A1* | 10/2005 | Faihe et al. | 714/25 |
| 2006/0242286 A1* | 10/2006 | Hawkins et al. | 709/223 |
| 2007/0220308 A1* | 9/2007 | Yeung et al. | 714/5 |
| 2007/0220365 A1* | 9/2007 | Castellani et al. | 714/46 |
| 2008/0126880 A1* | 5/2008 | Hegarty et al. | 714/46 |
| 2008/0195897 A1* | 8/2008 | Alaniz et al. | 714/46 |
| 2008/0300572 A1* | 12/2008 | Rankers et al. | 604/504 |
| 2009/0113248 A1* | 4/2009 | Bock et al. | 714/39 |

* cited by examiner

*Primary Examiner* — Scott Baderman
*Assistant Examiner* — Sarai Butler
(74) *Attorney, Agent, or Firm* — Lempia Summerfield Katz LLC

(57) ABSTRACT

A system and method provide system monitoring and detailed troubleshooting workflow guidance. Individual system components may be monitored and faulty system components identified. Subsequently, component-related, context-related, and/or user-specific troubleshooting workflow guidance associated with the faulty system component identified may be retrieved and/or determined by a processor and presented. The component-related guidance may be based upon which system component is faulty. The context-related guidance may be based upon the type of error with the faulty system component. The user-specific guidance may be based upon information specific to the user, such as user specifications, preferences, and configurations. The troubleshooting guidance may provide virtual guidance related to the workflow steps to be performed to identify the error with the faulty component and then correct the error identified. Accordingly, consistent, reproducible, and efficient troubleshooting may be performed using the troubleshooting workflow guidance presented. In one embodiment, the system monitored is a medical imaging system.

18 Claims, 5 Drawing Sheets

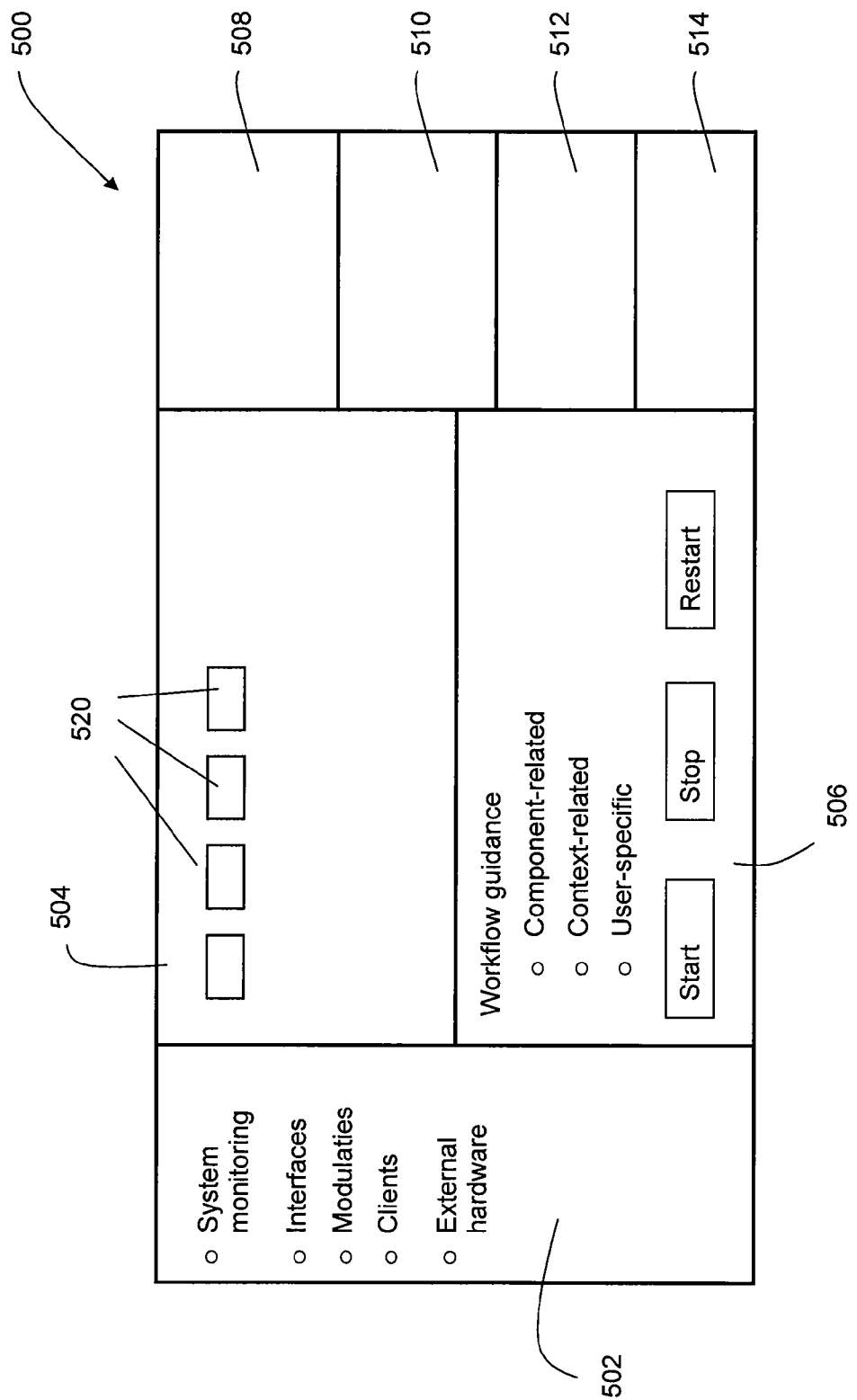

CONTEXT-RELATED TROUBLESHOOTING

BACKGROUND

The present embodiments relate generally to system monitoring. More particularly, the present embodiments relate to the identification and correction of system and/or system component faults and errors.

Information Technology (IT) systems may support a number of workflows performed by customer personnel at various customer locations, including workflows that utilize interactive software applications installed on customer computers, systems, and/or other machines. The IT systems may be directed toward a wide array of applications, including clinical workflows. As an example, the IT systems may assist medical personnel located at hospitals and other medical facilities to diagnose and treat patients. The systems and associated software applications may support medical imaging techniques and devices, and/or facilitate maintaining and updating medical files associated with individual patients. The systems may be directed toward other types of workflows as well, both medical and non-medical.

Existing IT systems may be monitored by conventional system monitoring software tools. However, inefficiencies and inconveniences may result from limitations associated with existing system monitoring tools. For instance, typical system monitoring tools may be limited to displaying only an overall system status. As a result, in response to generic system faults being detected by the system monitor, technicians attempting to remedy the situation may perform manually determined troubleshooting that is inefficient, inconsistent, and/or erroneous.

BRIEF SUMMARY

A system and method monitor the status of a system and/or associated system components. Faults with the system and/or individual components may be identified, and troubleshooting workflow guidance may be subsequently presented to a user. Component-related and/or context-related troubleshooting workflow guidance may be presented to the user. The component-related troubleshooting guidance may be component specific, and provide relevant information and/or tools necessary to correct an identified problem with the specific component. The context-related troubleshooting guidance may be error specific, and provide different error correction procedures and/or tools depending upon a specific error identified. Additionally or alternatively, user-specific troubleshooting may be presented to the user. The user-specific troubleshooting may be user specific, and provide different guidance for troubleshooting and error correction depending upon the user, such as procedures and tools specific to the user.

In one aspect, a method monitors a system and presents troubleshooting guidance. The method includes automatically monitoring system components of a system for faults using software, the software identifying a faulty system component. The method also includes presenting component-related troubleshooting workflow guidance associated with troubleshooting the faulty system component identified, the component-related troubleshooting workflow guidance including guidance that (1) is identified and/or retrieved by a processor based upon the faulty system component identified and (2) directs a number of workflow steps to be performed to troubleshoot the faulty system component.

In another aspect, a method monitors a system and presents troubleshooting guidance. The method includes automatically monitoring system components of a system for faults using software, the software identifying a faulty system component, and identifying a type of error associated with the faulty system component via a processor. The method also includes presenting context-related troubleshooting workflow guidance associated with the correction of the faulty system component that is specific to the type of error identified, the context-related troubleshooting workflow guidance including guidance that is (1) identified and/or retrieved by a processor and (2) related to a number of workflow steps to be performed to correct the type of error identified associated with the faulty system component.

In another aspect, a data processing system monitors a system and presents troubleshooting guidance. The system includes a memory unit operable to store virtual representations of workflow steps associated with troubleshooting a faulty system component, the workflow steps provide guidance (1) to identify a type of error with the faulty system component and (2) correct the error once identified. The system also includes a processing unit operable to monitor a system and identify the faulty system component within the system, and present the virtual representations of the workflow steps associated with troubleshooting the faulty system component on a display.

In yet another embodiment, a computer-readable medium provides instructions executable on a computer. The instructions direct monitoring system components associated with a user system and identifying a faulty system component. The instructions also include presenting user-specific troubleshooting workflow guidance that includes virtual guidance that guides the performance of a number of workflow steps associated with correcting the faulty system component, the user-specific troubleshooting workflow guidance being tailored based upon user specific information.

Advantages will become more apparent to those skilled in the art from the following description of the preferred embodiments which have been shown and described by way of illustration. As will be realized, the system and method are capable of other and different embodiments, and their details are capable of modification in various respects. Accordingly, the drawings and description are to be regarded as illustrative in nature and not as restrictive.

BRIEF DESCRIPTION OF THE DRAWINGS

FIG. 5 illustrates an exemplary user interface for presenting troubleshooting workflow guidance.

DETAILED DESCRIPTION

Figure 1:
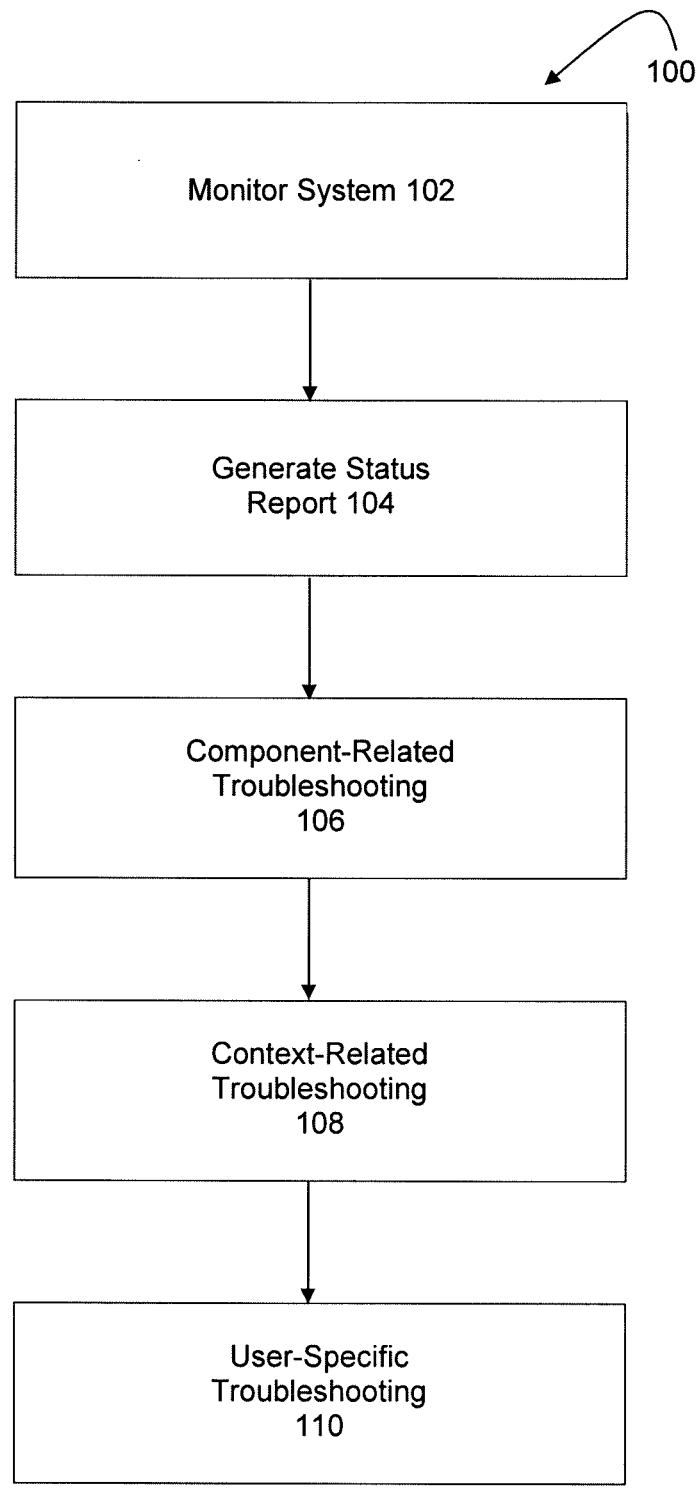
FIG. 1 illustrates an exemplary technique of monitoring a system and presenting troubleshooting workflow guidance for individual faulty system components.

The embodiments described herein include methods, processes, apparatuses, instructions, systems, or business concepts for monitoring a system and presenting detailed troubleshooting workflow guidance. A system having a number of system components may be monitored for faults. Individual faulty system components may be automatically identified by a processor. After a faulty component is identified, component-related, context-related, and/or user-specific troubleshooting workflow guidance associated with the faulty system component identified may be retrieved, identified, selected, and/or determined by the processor and presented to a user.

The component-related guidance may be component specific and provide troubleshooting workflow guidance based upon which system component is faulty. The context-related guidance may be error specific and provide troubleshooting workflow guidance based upon the type of error with the faulty system component. The user-specific guidance may be specific to the user and provide guidance based upon the user and/or user specifications, preferences, settings, configurations, and/or other information specific to the user.

As an example, the troubleshooting workflow guidance may provide guidance related to a number of workflow steps to be performed to (1) first identify the error with the faulty system component identified and (2) then correct the error identified. If the fault identified is only determined in relation to the system in general, the workflow guidance also may include workflow steps that may be performed to identify the faulty system component within the system. Reproducible and consistent troubleshooting may be performed following the virtual workflow guidance retrieved, selected, and/or identified by a processor and presented to the user, such via a display screen or hardcopy printout. As a result, limitations, inefficiencies, and/or ineffectiveness associated with conventional monitoring systems may be alleviated.

Information Technology (IT) and other systems may be monitored by conventional system monitoring tools, such as software monitoring tools. However, troubleshooting has conventionally been viewed as an individual item, separately from system monitoring. Therefore, conventional system monitoring tools may not provide the capability of correcting possible faults/errors by means of guided, component-related troubleshooting. Rather, typical monitoring tools may be limited to displaying a collective or overall status of the system monitored.

Standard monitoring tools may not offer component specific status monitoring or component specific interpretation of faults detected. Additionally, conventional monitoring tools may not identify the type of, or otherwise analyze, the faults detected, or offer troubleshooting guidance related to the correction of the faults detected. The present embodiments address these and other drawbacks.

In one aspect, system components may be monitored with a system monitoring tool. An individual system component may report a problem to the system monitoring tool. After which, the system monitoring tool may retrieve additional information related to the problem and/or a problematic system component, such as expanded component-related information for possible use during troubleshooting and error correction. The component-related information may be related to actions to be performed during troubleshooting and repair, a detailed explanation of the component and/or problem, and other information. The complete information collected by the system monitoring tool may be temporarily stored in a so-called "message repository," or other database, in a message format.

An automatic regulating mechanism, such as either a processor or a software application, may assess and generate a message based upon the complete information stored in the repository, such as an error message related to the status of the problematic system component. The component status may be presented graphically, textually, or via other various virtual views by a system monitoring user interface.

Subsequently, the user interface may present a troubleshooting procedure to be performed. The troubleshooting procedure may be tailored depending upon the intended role or involvement of the user in the performance of the troubleshooting and/or repair procedure. For instance, the procedure may be performed partially or fully by the user. In one aspect, the procedure may identify faulty parts that need to be replaced by a service technician. In another aspect, the faulty parts may be replaced by the user by following the troubleshooting and repair guidance, and/or software or hardware test tools.

Alternatively or additionally, the troubleshooting and/or repair procedure may be component specific and/or error specific. For instance, the procedure may use component specific analysis tools, calibration tools, test tools, functional descriptions, and/or troubleshooting guides. Other troubleshooting procedures and guidance may be determined and presented.

In one aspect, the system monitored may support clinical workflows that medical personnel located at hospitals and other medical facilities employ to diagnose and treat patients. As an example, the systems monitored may be associated with medical imaging systems and devices. The systems monitored may be directed toward other types of applications as well, both medical and non-medical.

I. Exemplary System Monitoring and Troubleshooting Techniques

FIG. 1 illustrates an exemplary method of monitoring a system and presenting troubleshooting workflow guidance 100. The method 100 may include monitoring a system 102, generating a system status report 104, presenting component-related troubleshooting workflow guidance 106, presenting context-related troubleshooting workflow guidance 108, and presenting user-specific troubleshooting workflow guidance 110. The method may include additional, fewer, or alternate steps.

The method 100 may include monitoring a system 102. The system may include a number of system components. The system components may be hardware, software, and/or other components. The system components may be integrated to perform a functional objective. The system and/or individual system components may be automatically monitored, such as via processor using a software tool. The software tool may run diagnostic tests and identify individual system components with actual or potential faults. The faults may indicate that an individual system component is not performing as expected, properly, optimally, or at all. Known system monitoring techniques may be used. Alternatively, the system and/or individual system components may be manually monitored. Other system/component monitoring may be performed and alternate monitoring tools may be used.

The method 100 may include generating a system status report 104. A system monitoring tool may generate a status report. The status report may be based upon the actual or possible faults identified with individual system components, such as via a processor running a software monitoring tool. The status report may include a display of an overall system status and/or the status of individual components.

As an example, a block diagram of interconnected system components may be virtually represented and displayed. A graphical depiction of the system and/or individual components may be presented. Alternatively, a text listing of individual components and/or sub-components may be presented.

The status of each interconnected component also may be visually depicted, such as graphically or textually. For instance, color coded status information may be presented for each individual component, such as green for no problem associated with the component, yellow for a potential problem or less than optimal performance, and red for a problem or fault detected. Alternatively or additionally, a textual report may be presented that textually details the status of each component. Other status reports may be generated.

The method 100 may include presenting troubleshooting or diagnostic workflow guidance, such as component-specific, error-specific, and/or user-specific workflow guidance. The workflow guidance presented may be predetermined and retrieved by a processor. Alternatively or additionally, the processor may identify, select, or otherwise determine a number of individual work steps to be included within a troubleshooting workflow presented. The workflow guidance may be automatically presented without user input, or only after a user input operation is entered. An exemplary user input operation may be performed using a keyboard or clicking a mouse, such as selecting a virtual representation of a component identified as faulty on a display screen.

A processor may select work steps to be included within a tailored workflow based upon one or more variable conditions. The variable conditions may depend on the type of system monitored, the faulty component, the type of error, user specific information, and/or other conditions. For instance, the processor may select appropriate work steps that account for a particular component overheating, a particular component not responding to commands sent by a controller or processor, user preferences, and/or other conditions, including those discussed elsewhere herein.

In one aspect, predetermined and/or benchmarked troubleshooting workflow guidance, comprising either complete or partial workflows, may be stored in a database. The workflows may be stored as complete workflows to be performed or individual work steps that may selected by the processor during real-time to dynamically create a full workflow.

In another aspect, benchmarked or other troubleshooting workflows may be virtually represented on a display. In general, benchmarking is a process that may improve processes or workflows. Benchmarking may involve identifying, understanding, and adapting outstanding practices from organizations located around the globe to improve performance. Benchmarking may look to find the so-called "best practices" having the optimal performances, as well as measure actual workflows currently being used against the best practices.

Accordingly, a number of troubleshooting related workflow steps, or even complete troubleshooting workflows, specific to system components, particular errors or types of errors, and/or users may be predetermined and benchmarked. The workflows and/or workflow steps identified by the benchmarking process may then have associated virtual machine representations created by a software expert. Each troubleshooting workflow or portion thereof developed may be converted to a machine readable representation, a computer file, digital data, or other computer related or virtual representation/description. The virtual representations of the workflow steps may be stored in a database for subsequently retrieval, selection, and/or presentation to the user via a user interface.

Referring back to FIG. 1, the method 100 may include presenting component-related troubleshooting guidance 106. The component-related guidance may be component specific and provide troubleshooting workflow guidance based upon which system component is faulty.

The method may include presenting component-related troubleshooting workflow guidance associated with (1) the identification of the faulty system component, (2) the identification of an error associated with the faulty system component, and/or (3) the correction of the error identified. The workflow guidance presented directing the correction of the error identified may include guidance directing (3a) the identification of a faulty part of the faulty component, (3b) the replacement of the faulty part, and (3c) testing the system and/or faulty component after the faulty part has been identified and replaced.

The component-related troubleshooting workflow guidance may include workflow guidance that is (1) retrieved from a memory, or identified, selected, or otherwise determined by a processor, and (2) related to or directs a number of workflow steps to be performed to troubleshoot the faulty system component. The workflow guidance may include a number of workflow steps to be performed that relate to first identifying the error associated with the faulty system component and then a number of workflow steps to be performed that relate to the correction or repair of the error identified.

The workflow steps needed to identify the error with the faulty system component may depend on the type, make, or model of the faulty system component, and/or user specifications, such as settings or configurations. The workflows steps may be predetermined and retrieved from a memory, or dynamically selected during runtime, by a processor. For instance, a processor may modify the work steps to be performed based upon various conditions, such as conditions automatically monitored by the system monitoring tool. Conditions monitored may include temperatures, levels, voltages, currents, and/or other system or component measurable parameters.

After the error with the faulty component is identified, the system may present workflow steps to correct or repair the component. The workflow steps to correct the error may be predetermined or selected by a processor during runtime based upon various conditions automatically monitored by the processor, such as those mentioned above. The workflow steps to correct the component may involve replacing a faulty part of the component identified as being the cause of the fault and then testing the faulty component with the replacement part.

The method 100 may include presenting context-related troubleshooting guidance 108. The context-related guidance may be error specific and provide troubleshooting workflow guidance based upon the type of error with the faulty system component. The error specific workflow guidance may be predetermined and retrieved from a memory, or dynamically selected at runtime, by a processor based upon various conditions automatically monitored by the processor. The error specific guidance may involve the replacement and testing of predetermined parts with a likely chance of being the cause of the fault.

The method 100 may include presenting user-specific troubleshooting guidance 110. The user-specific guidance may be user specific and provide guidance based upon the user and/or user specifications, preferences, settings, and/or configurations. The user-specific workflow guidance may be predetermined and retrieved from a memory, or dynamically selected at runtime, by a processor based upon various conditions automatically monitored by the processor. The user-specific guidance may involve replacing a suspect part and configuring the system and/or faulty component in accordance with user specifications, settings, and/or operational preferences.

II. Exemplary System for Monitoring and Guiding Troubleshooting

Figure 2:
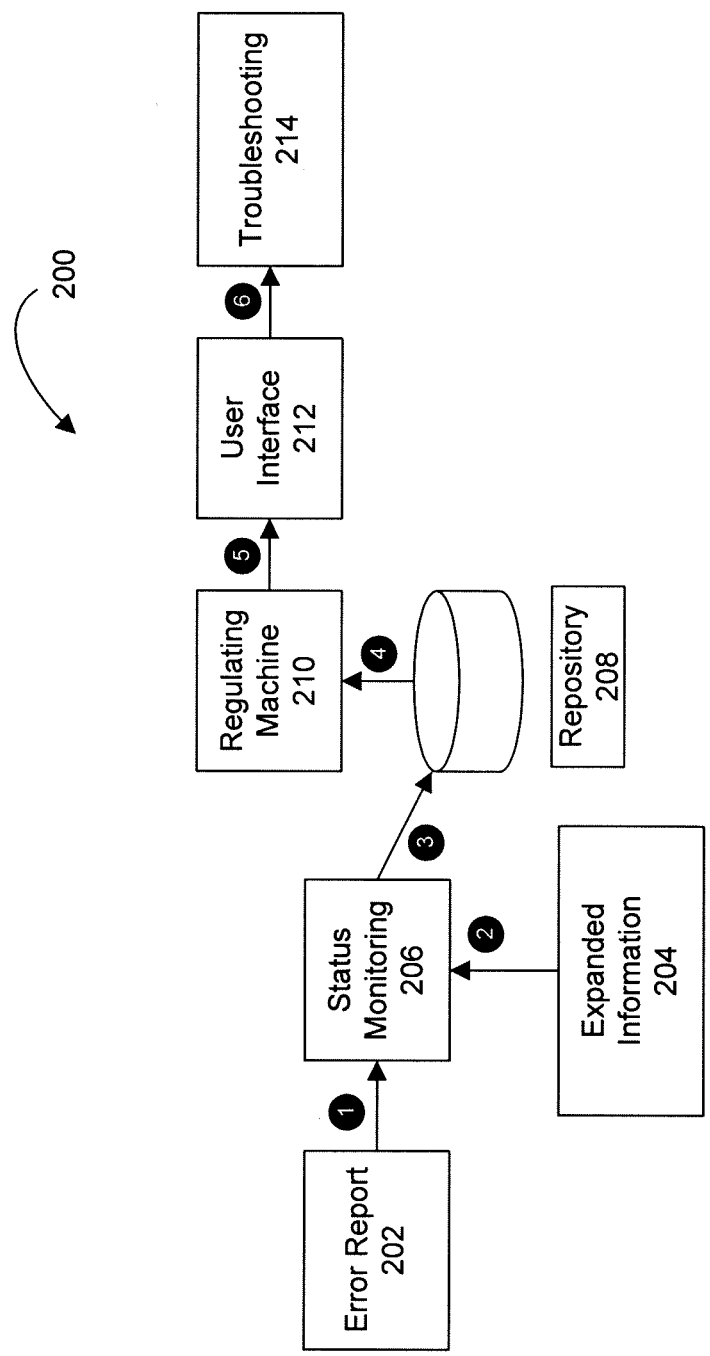
FIG. 2 illustrates an exemplary system for monitoring a system and presenting troubleshooting workflow guidance for individual faulty system components.

FIG. 2 illustrates an exemplary system for monitoring a system and presenting troubleshooting workflow guidance 200. The system 200 may generate error reports 202, include a database of expanded information 204, monitor system status 206, provide a repository 208, a regulating machine 210, and a user interface 212, and facilitate troubleshooting 214. The system may include additional, fewer, or alternate components and functionality.

A system may include a number of hardware and/or software components. Individual system components may be automatically monitored by a processor and/or a system monitoring software tool. In one aspect, the system monitoring tool may be based upon windows, unix, linux, or another operating system. Other software tools may be used.

Individual system components may report faults or problems 202 to the system monitoring tool 206. Alternatively, the system monitoring tool 206 may automatically identify faulty or problematic individual components. The problem identified or collected by the system monitoring tool 206 may be expanded, or expounded upon, by a component-related piece of information associated with troubleshooting and/or error correction that is stored in a database of expanded information 204.

The component-related piece of information may detail actions or troubleshooting work steps to be performed, include an extensive explanation of the component and/or problem, and/or include other system, component, or troubleshooting related information. The complete information collected by the system monitoring tool 206 may be stored in a so-called message repository 208. The message repository 208 may be a database of messages and/or other troubleshooting related files.

An automatic regulating mechanism 210 may be a software tool or a separate processor. The automatic regulating mechanism 210 may automatically assess or monitor the complete information stored in the repository and generate appropriate messages detailing possible problems and/or problem correction mechanisms, such as those described herein.

The assessed status data, as determined by the automatic regulating mechanism 210, may be shown to the user, such as graphically and/or textually via a user interface 212. The assessed status may depict information related to the role of the user, such as what actions the user is to perform, during the troubleshooting process. The assessed status may be presented in a number of different types of summary views of the system via the system monitoring user interface 212.

Subsequently, the user may be introduced directly from the system monitoring user interface to the troubleshooting workflow guidance 214. For instance, the user interface may be operable to present a number of hierarchal levels. The upper most level or levels may relate to system monitoring, while the lower or drill-down levels may relate to the presentation of troubleshooting workflow guidance. The user may be presented role-based and/or component-specific analysis tools. Additionally or alternatively, the user may be presented with calibration tools, test tools, functional descriptions, troubleshooting guides, repair procedures and techniques, and/or other troubleshooting related information.

The troubleshooting workflow guidance 214 may include virtual representations of work steps created by a software expert. The software expert may create virtual representations of benchmarked workflows or individual work steps and place the virtual representations in a new or an existing database. The database of troubleshooting workflow guidance created may provide an efficient manner of providing benchmarked troubleshooting workflows or work steps to customers, such as via remote distribution of the virtual workflows over a communications network. In other words, the troubleshooting workflows may provide a mechanism for the efficient transfer of knowledge from an organization with extensive expertise and experience to remote facilities with only limited resources and personnel having less experience related to troubleshooting and repairing complex integrated systems, such as IT and/or medical systems.

New technology also leads to the creation of new systems that experience new problems and require new troubleshooting procedures. The troubleshooting workflows discussed herein may present solutions to those problems. For instance, the troubleshooting workflows discussed herein may provide an efficient manner of transferring the knowledge gained by the facilities that have already experienced the "growing pains" associated with troubleshooting and repairing new types of systems and equipment. As a result of the present embodiments, an optimal manner of troubleshooting and repairing new equipment may be easily relayed to facilities subsequently acquiring that new equipment without those facilities having to inefficiently "re-invent the wheel."

The troubleshooting workflows may be optimized and stored in a machine readable virtual form that includes a reproducible written description, graphical depiction, table, text, article, flowchart, video, audio tape, and/or other virtual or machine readable representation of the best way of performing that workflow. For example, a graphic, table, or other visual representation may be presentable to the user that displays the process steps (such as a graphic depiction of one or more of the work steps, along with associated textual and/or audio information related to the work steps).

As noted, a processor may identify individual workflow steps from a predetermined workflow to present to the user. The individual workflow steps selected may be based upon user-specific information, such as type of system or system components employed, or upon various systems conditions automatically monitored by the system monitoring tool.

As an example, the systems monitored may employ interactive software applications that rely upon customer specifications, such as customer protocols, to properly run various pieces of equipment. The customer protocols may account for hardware and hardware configurations, as well as the customer's software configurations. The customer protocols may include all settings and parameters related to the type of computers and/or machines that the software application operates on at the customer location. In one embodiment, the customer specific data may include all of the individual customer data and settings used by a software application, such as an application that controls a medical imaging device.

The troubleshooting workflow guidance may be tailored by a processor, such as by selecting, modifying, adding, or deleting various work steps, based upon the customer specifications and protocols. For example, based upon the customer specific data received by a processor or system monitoring tool, a troubleshooting workflow may be automatically or manually modified to account for the customer specific data pertinent to the customer system. After generating the tailored troubleshooting process, a graphical, textual, computer, video, audio, or combination of thereof, and/or other virtual representation of the tailored troubleshooting process may be generated to illustrate the proper performance of the tailored troubleshooting process to the user.

In one aspect, the processor or system monitoring tool may employ a number of tables and/or predetermined rule sets. The rules may correlate faulty components and/or specific errors identified with the customer related data, such as settings, specifications, customizations, and functionality. As a result, work steps required to re-configure the system in accordance with the customer specifications may be identified by the processor/system monitoring tool and presented to the user. Other troubleshooting and repair work steps may be automatically identified by a processor or software tool.

The troubleshooting guidance may include testing the system and/or component after troubleshooting and/or repair. A number of tests may be automatically performed by a software tool. For instance, the software tool may check that a system or faulty component has been modified to properly account for the customer related data, such as the customer specific data and/or customer protocols. Alternatively or additionally, a number of tests may be performed manually with the assistance of the workflow guidance presented. If the software associated with a faulty component is replaced during troubleshooting, an executable version of the modified software may be automatically or semi-automatically tested. Any problems with the modified software may be automatically or manually identified and troubleshot further, such as via separate workflow guidance identified by the processor.

III. Exemplary Data Structures

Figure 3:
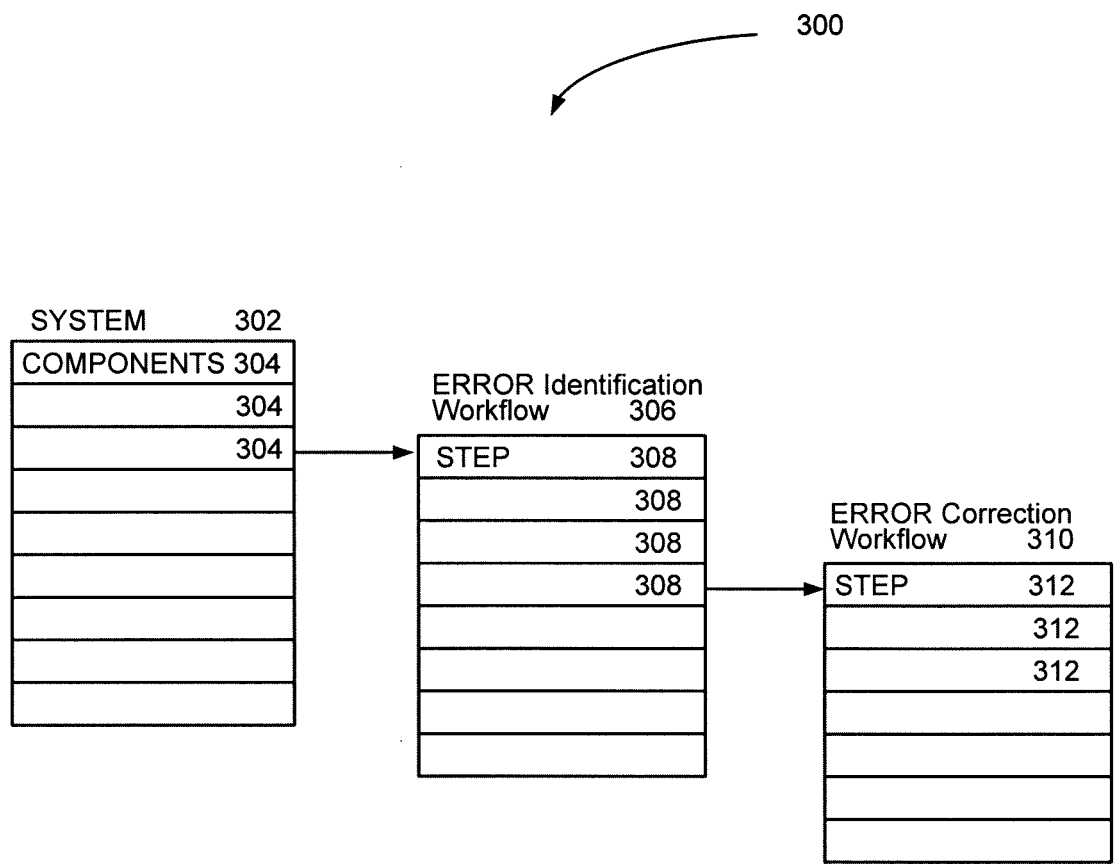
FIG. 3 illustrates exemplary troubleshooting workflow guidance data structures.

FIG. 3 illustrates exemplary database structures for storing virtual representations of troubleshooting workflow procedures 300. The data structures may include system related data structures 302, error identification workflow data structures 306, and/or error correction workflow data structures 310. Alternate, additional, or fewer data structures may be used. For instance, dedicated data structures related to the component-related, context-related, and/or user-specific information discussed herein may be used.

In general, the data structures may be statically or dynamically created. The data structures may be predetermined and stored in read only memory. Alternatively or additionally, the data structures may be built during runtime in real time and stored in RAM. The data structures may be lists, queues, arrays, multi-dimensional arrays, tables, trees, b-trees, node lists, or other data structures.

As shown, the exemplary data structures include a system dedicated data structure 302. The system data structure 302 is a list of virtual system components 304. For example, with a C-arm imaging system, the system components may include the C-arm, mount, source, detector, monitor, patient table, interconnected processors, modules, interfaces, servers, and other components. Each virtual system component 304 may include a pointer to a corresponding error identification workflow 306.

For instance, if a user software module is determined to be the individual faulty system component 304, a dedicated virtual workflow 306 may be presented to the user that is intended to identify the error or type of error with the component 304 (the user software module in our example).

The dedicated error identification workflow 306, corresponding to the individual system component identified as being faulty, may include one or more predetermined or dynamically determined workflow steps 308. Each virtual workflow step in the error identification workflow 306 may include a pointer to a corresponding error correction workflow 310. Each error correction workflow 310 may include one or more virtual workflow steps 312 associated with correcting the corresponding error.

In one embodiment, as depicted by FIG. 3, a database may include data related to a system being monitored. The data may be organized by system component. Each system component data structure or file may include a pointer or link to a component-specific workflow virtual representation that includes a machine representation of one or more workflows or work steps to be followed to facilitate the identification of a specific error or error type with the system component. The error identification workflow data structure may include a pointer or link to an error correction workflow data structure. Once the type of error is identified, the workflow detailing workflow steps to be performed to correct the error identified may be retrieved and displayed.

IV. Exemplary Data Processing System

Figure 4:
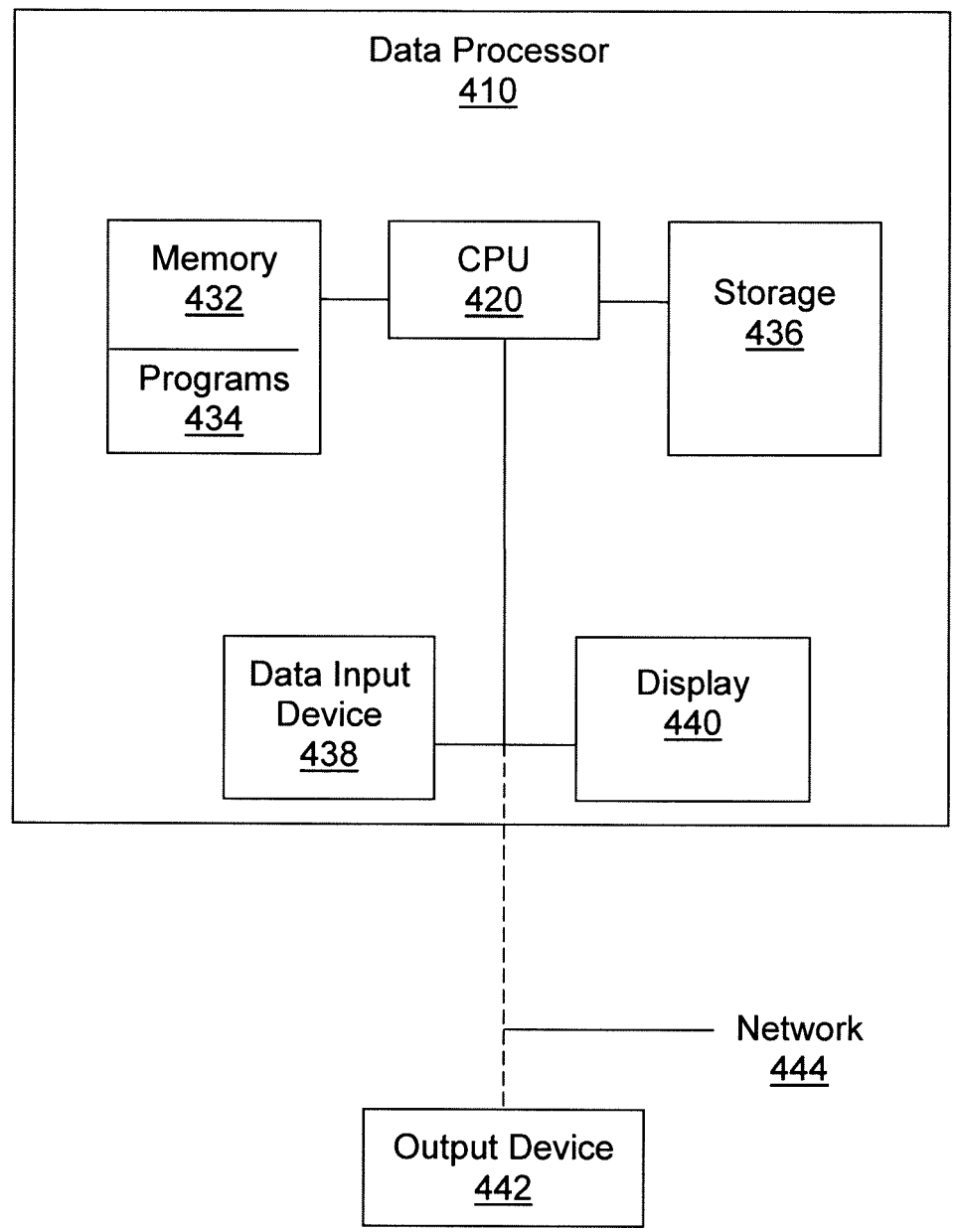
FIG. 4 illustrates an exemplary data processor configured or adapted to provide the functionality for monitoring a system and presenting troubleshooting workflow guidance for individual faulty system components.

FIG. 4 illustrates an exemplary data processor 410 configured or adapted to provide the functionality for monitoring a system and presenting troubleshooting workflow guidance. The data processor 410 may be located at a customer location with a system to be monitored. The data processor 410 may include a central processing unit (CPU) 420, a memory 432, a storage device 436, a data input device 438, and a display 440. The processor 410 also may have an external output device 442, which may be a display, a monitor, a printer or a communications port. The processor 410 may be a personal computer, work station, or other processing system. The processor 410 may be interconnected to a network 444, such as an intranet, the Internet, or an intranet connected to the Internet. The processor 410 may be interconnected to a customer system or a remote location via the network 444. The data processor 410 is provided for descriptive purposes and is not intended to limit the scope of the present system. The processor may have additional, fewer, or alternate components.

A program 434 may reside on the memory 432 and include one or more sequences of executable code or coded instructions that are executed by the CPU 420. The program 434 may be loaded into the memory 432 from the storage device 436. The CPU 420 may execute one or more sequences of instructions of the program 434 to process data. Data may be input to the data processor 410 with the data input device 438 and/or received from the network 444 or customer system. The program 434 may interface with the data input device 438 and/or the network 444 or customer system for the input of data. Data processed by the data processor 410 may be provided as an output to the display 440, the external output device 442, the network 444, and/or stored in a database.

The program 434 and other data may be stored on or read from a machine-readable medium, including secondary storage devices such as hard disks, floppy disks, CD-ROMS, and DVDs; electromagnetic signals; or other forms of machine readable medium, either currently known or later developed. The program 434, memory 432, storage unit 436, and other data may comprise and store a database of machine readable files and data associated with system monitoring, system components, and troubleshooting workflow guidance. The database may store troubleshooting workflow guidance as discussed herein including component-related, context-related, and user-specific troubleshooting.

The data processing system may include a memory unit operable to store virtual representations of workflow steps associated with troubleshooting a faulty system component. The workflow steps may provide guidance (1) to identify a type of error with the faulty system component and/or (2) correct the error once identified. The data processing system also may include a processing unit operable to monitor a system and identify the faulty system component within the system, and present the virtual representations of the workflow steps associated with troubleshooting the faulty system component on a display. The virtual representations may include audio and video instructions that facilitate the identification of the type of error and/or the correction of the error once identified. The processing unit may alter the virtual representations of the workflow steps presented based upon user specific information.

The data processing system may access a computer-readable medium having instructions executable on a computer stored thereon. The instructions may direct monitoring system components associated with a user system; identifying a faulty system component; and presenting user-specific troubleshooting workflow guidance that includes virtual guidance that guides the performance of a number of workflow steps associated with correcting the faulty system component. The user-specific troubleshooting workflow guidance may be tailored based upon user specific information. The instructions also may direct selecting the user-specific troubleshooting workflow guidance based upon a type of the user system, a type of faulty system component identified, and/or other criteria, such as that discussed elsewhere herein. The instructions may direct selecting user-specific troubleshooting workflow guidance based upon stored user specifications, preferences, configurations, and/or other user specific information.

In one embodiment, the data processor 410 may be operable to automatically or semi-automatically monitor system components of a system. The processor 410 may modify a predetermined troubleshooting workflow presented, such as a standard workflow for a given type of component, to account for user customizations, specifications, machines, configurations, settings, preferences, and other user specific items. The modified troubleshooting workflow may be presented to the user via a display or printout. A virtual troubleshooting workflow (in digital data or machine readable form) may be received by the data processor 410 from the database, data input device 438, the network 444, or another input device. After which, the data processor 410 may revise the workflow to create a virtual modified workflow (in digital data or machine readable form) that may be stored in the memory 432, the storage device 436, or other storage unit.

V. Exemplary User Interface

A user interface may present the troubleshooting workflow guidance to a user. The user interface may present a number of different level views of the system and system components. The user interface may provide access to a component view, a functional view, and a fault diagnosis view. The user interface may provide access to a hierarchical view and a status view, the status view may present system status and various messages. The user interface may present additional, fewer, or alternative views.

FIG. 5 illustrates an exemplary user interface for presenting troubleshooting workflow guidance 500. The user interface 500 may include a tree structure window 502, a topogram window 504, a details window 506, a notepad window 508, a knowledge base window 510, a ticket handling window 512, and a message ticket window 514. The user interface may include additional, fewer, or alternate components.

FIG. 5 depicts an exemplary wireframe of a Troubleshooting Page. The Troubleshooting Page may contain several frames and/or tools. The user may be able to navigate through the Troubleshooting Page and associated portals and links. For instance, there may be a number of tabs, buttons, or menus accessible at the top of the display screen associated with displaying the Troubleshooting Page, such as a dedicated Troubleshooting Tab or Button that provides access to troubleshooting workflow guidance functionality.

The tree structure window 502 may provide a structured view of all system components. The tree structure window 502 may be correlated with the topogram window 504, which may display representations of the same components.

The topogram window 504 may be a graphical view of all system components. For instance, each system component may be represented by an icon. In one embodiment, the system components virtually represented may include a system monitoring tool, client computers/machines, modalities, interfaces, and external hardware. If one of the icons representing a system component is clicked or double clicked upon, a lower level page associated with that component may be presented. The lower level component display may display sub-components of the components, such as a main server or an additional server that may be associated with a system monitoring tool.

The details window 506 may display information related to an individual component selected from either the tree structure window 502 or topogram 504. The notepad window 508 may provide the user with the option of entering some notes during the troubleshooting workflow for subsequent analysis. The knowledge base window 510 may provide access to a separate pop-up window that facilitates network access to more detailed information. The ticket handling window 512 may provide for opening IT related tickets associated with system and component problems. The message ticket window 514 may provide functionality associated with tracking the status of open IT ticket items.

When an icon displayed in the topogram window 504 or a component text item displayed in the tree structure window 502 is selected by a user, the next hierarchical level may displayed. In the next hierarchical level, the subcomponents and related information may be displayed. Additionally, in one aspect, the health status details of the selected component may then be displayed in the details window 506. The health status details may be related to component fan speed, system or component temperature, CPU temperature, and/or other parameters monitored.

The tree structure box 502 may display a text list of system components. In one aspect, the high level system components may include the system monitoring tool, interfaces, modalities, client devices, and external hardware. By clicking upon one of the high level components, a list of associated subcomponents may be displayed.

As an example, the system monitoring tool may have two main subcomponents, such as a main server and additional server, which in turn each have additional lower level components. For instance, the main server may have associated server, graphic card, network, operating system, database, backup, application server, display server, and/or other subcomponents. By performing a user operation on one of the components or subcomponents, such as by clicking with a mouse, detailed troubleshooting guidance related to the component or subcomponent, respectively, may be presented in the details window 506.

The topogram box 504 may display a number of system component related icons. By performing a user operation on one of the components, a lower level display may be displayed of associated subcomponents. As an example, by clicking upon the system monitoring tool, a table or other graphic representation of the associated server, graphic card, network, operating system, database, backup, application server, display server, and/or other subcomponents may be displayed.

The details window 506, at a high level, may present a system overview. The details window 506 may present a list of assets, such as the system monitor, modalities, interfaces, client devices, and other hardware and software assets.

As an example, if the system monitoring tool determines that the CPU temperature of a server is too high, the monitoring tool decides which color the server is to be displayed as. For example, the color of a faulty component may be emphasized or otherwise highlighted visually.

If the server is part of a system component having other servers for load balancing, such that the system component is still functional, the problematic server itself may be highlighted in red if it is not working any longer. On the other hand, the related system component may be displayed yellow in the first level of the topogram if the component is still operational, although at a reduced capacity. Furthermore, the affected or problematic component and subcomponent may be highlighted in the tree structure window 502 and on a first level of the details window 506.

During use, the lower levels of the details window 506 may present the component-related, context-related, and user-specific workflow guidance discussed herein. One of the lower levels of the details window 506 also may present a list of conditions and/or subcomponents associated with a monitored component. For example, for a server component, the details window 506 may present the associated fan speed, system temperature, CPU temperature, and other conditions. A visual depiction of the conditions monitored may be displayed. Other component conditions may be monitored and virtually represented.

The details window 506 may include a number of buttons associated with the presentation of workflow guidance. In embodiment, start, stop, and restart buttons may be displayed that move forward and backward within the work steps associated with the workflow guidance and being displayed.

The details window 506 may present function guide, test tools, and message viewer related buttons. The function guide button may provide access to all information about the functionality of the component that was selected from the upper level display for troubleshooting workflow. Information also may be presented that details the component's interaction with the other interconnected components.

The test tools button may provide access to applicable software test tools or instructions for using either applicable software or hardware test tools. The test tool buttons may present guidance related to the user's role in the troubleshooting workflow to find and solve a problem. The test tools may provide the user with the functionality to perform the component and context based troubleshooting discussed herein.

The message viewer button may provide access to filtered messages directed toward the component selected from the higher level display for troubleshooting. The details window may include additional, fewer, or alternate functionality.

VI. Exemplary Systems to be Monitored

In the aspect that the systems monitored are directed toward the medical field, the customer locations may be hospitals, clinics, or other medical facilities. The customer personnel may include doctors, nurses, and other medical personnel. The systems monitored may assist the medical personnel with the diagnosis of medical conditions and the treatment of patients.

The systems monitored may be facilitate clinical workflows, including processing images illustrating an enhanced region of interest within a patient. For example, various types of contrast medium may be administered to a medical patient. The contrast mediums enhance the scans acquired by scanning a patient or images of the patient, the scans and images may be recorded by an external recording device as enhancement data. The contrast medium typically travels through a portion of the body, such as in the blood stream, and reaches an area that medical personnel are interested in analyzing. While the contrast medium is traveling through or collected within a region of interest, a series of scans or images of the region of interest of the patient may be recorded for processing and display by the software applications. The enhanced region of interest may show the brain, the abdomen, the heart, the liver, a lung, a breast, the head, a limb or any other body area.

The systems monitored may acquire images or scans of the patient. The systems monitored may include radiography, angioplasty, computerized tomography, ultrasound and magnetic resonance imaging (MRI) systems. Additional types of systems monitored may include perfusion and diffusion weighted MRI, cardiac computed tomography, computerized axial tomographic scan, electron-beam computed tomography, radionuclide imaging, radionuclide angiography, single photon emission computed tomography (SPECT), cardiac positron emission tomography (PET), digital cardiac angiography (DSA), and digital subtraction angiography (DSA) systems. Alternate systems may be monitored.

In one aspect, the system monitored may have customer protocols or other customer specific data dependent upon the type of imaging process(es) or imaging processing device that the software application supports. The customer protocols may comprise all of the settings for the operating machines and medical imaging modules and subroutines associated with the software application in order to generate medical image data. The settings may be manufacturer, supplier, or distributor specific or may be customized by the customer. For example, the customer protocols may account for the type of machine used by the customer and/or comprise settings for magnetic resonance imaging devices, computer tomography devices, and other imaging devices, including, but not limited to, devices pertaining to the imaging processes mentioned directly above.

The troubleshooting workflows may account for the customer specific data and protocols. Additionally, some institutions may be relatively inexperienced with troubleshooting medical imaging devices. Providing standardized troubleshooting procedures to perform with medical imaging systems experiencing problems may alleviate inefficient, unguided, and uninformed troubleshooting, which may waste resources or damage equipment.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

It is therefore intended that the foregoing detailed description be regarded as illustrative rather than limiting, and that it be understood that it is the following claims, including all equivalents, that are intended to define the spirit and scope of this invention.

What is claimed is:

1. A method of monitoring a system and presenting troubleshooting guidance, the method comprising:

automatically monitoring system components of the system for faults using software, the software identifying a faulty system component; and presenting component-related troubleshooting workflow guidance associated with troubleshooting the faulty system component identified, the component-related troubleshooting workflow guidance including guidance that (1) is identified and/or retrieved by a processor based upon the faulty system component identified and (2) directs a number of workflow steps to be manually performed to troubleshoot the faulty system component and identify an error associated with the faulty system component, wherein the component-related troubleshooting workflow guidance includes guidance that is automatically selected by the processor based upon user specific information, and wherein the component-related troubleshooting workflow guidance further includes guidance that directs a number of workflow steps to be manually performed to identify a faulty part of the faulty system component, replace the faulty part, and test the system and the faulty component after the faulty part has been identified and replaced; and automatically modifying one or more of the number of workflow steps based upon conditions of the system or the system components, wherein the conditions include temperatures, voltages, and currents.

2. The method of claim 1, wherein the component-related troubleshooting workflow guidance presented includes information regarding an implementation of a component-specific analysis tool to facilitate identification of the error associated with the faulty system component.

3. The method of claim 1, wherein the component-related troubleshooting workflow guidance presented includes graphical representations of the workflow steps to be performed to troubleshoot the faulty system component.

4. The method of claim 1, wherein the component-related troubleshooting workflow guidance includes audio and video guidance regarding a performance of the workflow steps to be performed to troubleshoot the faulty system component.

5. The method of claim 1, wherein the component-related troubleshooting workflow guidance includes guidance that is automatically selected by the processor based upon a type of error identified with the faulty system component and directs correction of the type of error identified.

6. The method of claim 1, wherein the system monitored for faulty system components is a medical imaging system.

7. A method of monitoring a system and presenting troubleshooting guidance, the method comprising:

automatically monitoring system components of the system for faults using software, the software identifying a faulty system component;

identifying a type of error associated with the faulty system component via a processor;

presenting context-related troubleshooting workflow guidance associated with correction of the faulty system component that is specific to the type of error identified, the context-related troubleshooting workflow guidance including guidance that is (1) retrieved and/or identified by the processor and (2) related to a number of workflow steps to be manually performed to correct the type of error identified associated with the faulty system component; and automatically modifying one or more of the number of workflow steps based upon conditions of the system or the system components, wherein the conditions include temperatures, voltages, and currents.

8. The method of claim 7, wherein the context-related troubleshooting workflow guidance includes guidance based upon a type of faulty system component identified.

9. The method of claim 7, wherein the context-related troubleshooting workflow guidance includes graphical representations of the workflow steps to be manually performed to correct the type of error identified.

10. The method of claim 7, wherein the context-related troubleshooting workflow guidance includes audio and video guidance directing a performance of the workflow steps to be manually performed to correct the type of error identified.

11. The method of claim 7, wherein the system monitored for faulty system components is a medical imaging system.

12. The method of claim 7, wherein the context-related troubleshooting workflow guidance further includes guidance related to a number of workflow steps to be manually performed to test the system and the faulty system component after the identified error has been corrected.

13. A data processing system for monitoring a system and presenting troubleshooting guidance, the system comprising:

a memory unit operable to store virtual representations of workflow steps associated with troubleshooting a faulty system component, the workflow steps provide guidance (1) to manually identify a type of error with the faulty system component and (2) manually correct the error once identified; and a processing unit operable to monitor the system and identify the faulty system component within the system, and present the virtual representations of the workflow steps associated with manually troubleshooting the faulty system component on a display, wherein the processing unit is further operable to automatically modify the virtual representations of the workflow steps based upon conditions of the system or system components, and wherein the conditions include temperatures, voltages, and currents.

14. The data processing system of claim 13, wherein the virtual representations include audio and video instructions that facilitate the identification of the type of error and the correction of the error once identified.

15. The data processing system of claim 13, wherein the processing unit alters which of the virtual representations of the workflow steps are presented based upon user specific information.

16. A non-transitory computer-readable storage medium having instructions executable on a computer stored thereon, the instructions comprising:

monitoring system components associated with a user system;

identifying a faulty system component;

presenting user-specific troubleshooting workflow guidance that includes virtual guidance that guides manual performance of a number of workflow steps associated with correcting the faulty system component, the user-specific troubleshooting workflow guidance being selected based upon user specific information, wherein the user-specific troubleshooting workflow guidance further includes guidance that directs identification of a faulty part of the faulty system component, replacement of the faulty part, and testing of the system and the faulty component after the faulty part has been identified and replaced; and automatically modifying one or more of the number of workflow steps based upon conditions of the user system or the system components, wherein the conditions include temperatures, voltages, and currents.

17. The non-transitory computer-readable storage medium of claim 16, the instructions comprising selecting the user-specific troubleshooting workflow guidance based upon a type of the user system and/or a type of faulty part identified.

18. The non-transitory computer-readable storage medium of claim 16, wherein the user system associated with the system components monitored is a medical imaging system.

* * * * *